(12) United States Patent
Naguib

(10) Patent No.: US 6,623,768 B1
(45) Date of Patent: Sep. 23, 2003

(54) **PHARMACEUTICALLY ACTIVE COMPOSITION EXTRACTED FROM *FERULA HERMONIS* AND PROCESS OF ITS EXTRACTION**

(76) Inventor: Yousry M. A. Naguib, 602 Fairview Ave., Apt. #31, Arcadia, CA (US) 91007

( * ) Notice: Subject to any disclaimer, the term of this patent is extended or adjusted under 35 U.S.C. 154(b) by 0 days.

(21) Appl. No.: 10/123,919

(22) Filed: Apr. 16, 2002

(51) Int. Cl.$^7$ .......................... A01N 65/00; A61K 35/78
(52) U.S. Cl. ..................................... 424/773
(58) Field of Search ......................... 424/773

(56) References Cited

PUBLICATIONS

Computer Abs AN 2001127586 EMBASE Diab et al "TI Daucane aryl esters composition from the Lebanese *Ferula hermonis* Boiss. (zallooh root)." Flavoour & Fragrance Jour (2001) 16/2 (120–122.*

Computer Abs 2001353298 EMBASE TI Separation and quantification of the major daucane esters of *Ferula hermonis* by HPLC. AU Abourashed et al Planta Medica (2001 67/7 (681–682).*

Computer Abs 2001412801 EMBASE Diab et al "2,3–<SYM97>–Eposyjaeschkeanadiol 5–benzoate from *Ferula hermonis* boiss." CS R. Dolmazon, Laboratoire de Chimie Organique, Domaine Scientifique de la Doua, Flavour & Frag Jour (2001) 16/6 (397–400).*

Computer Abs 2001008227 EMBASE TI Sesquiterpenes from *Ferula hemonis* Boiss. AU Galal A.SO Pharmazie, (2000) 55/12 (961–962).*

Computer Abs 2003171081 EMBASE A comparative study of *Ferula hermonis* root extracts and sildenafil on copulatory behaviour of male rats. Hadidi K.A. et al. CS T. Aburjai, Dept. Pathol., Microbiol./F., Fac Fitoterapia (2003) 74/3 (242–246).*

* cited by examiner

*Primary Examiner*—Herbert J. Lilling

(57) ABSTRACT

The present invention is directed toward a pharmaceutically active composition extracted from *Ferula hermonis* by a process comprising contacting *Ferula hermonis* with a supercritical carbon dioxide fluid at conventional supercritical fluid extraction temperatures and pressures, and for a time sufficient to remove the active composition from *Ferula hermonis*, and recovering the pharmaceutical active composition from the supercritical fluid.

12 Claims, 1 Drawing Sheet

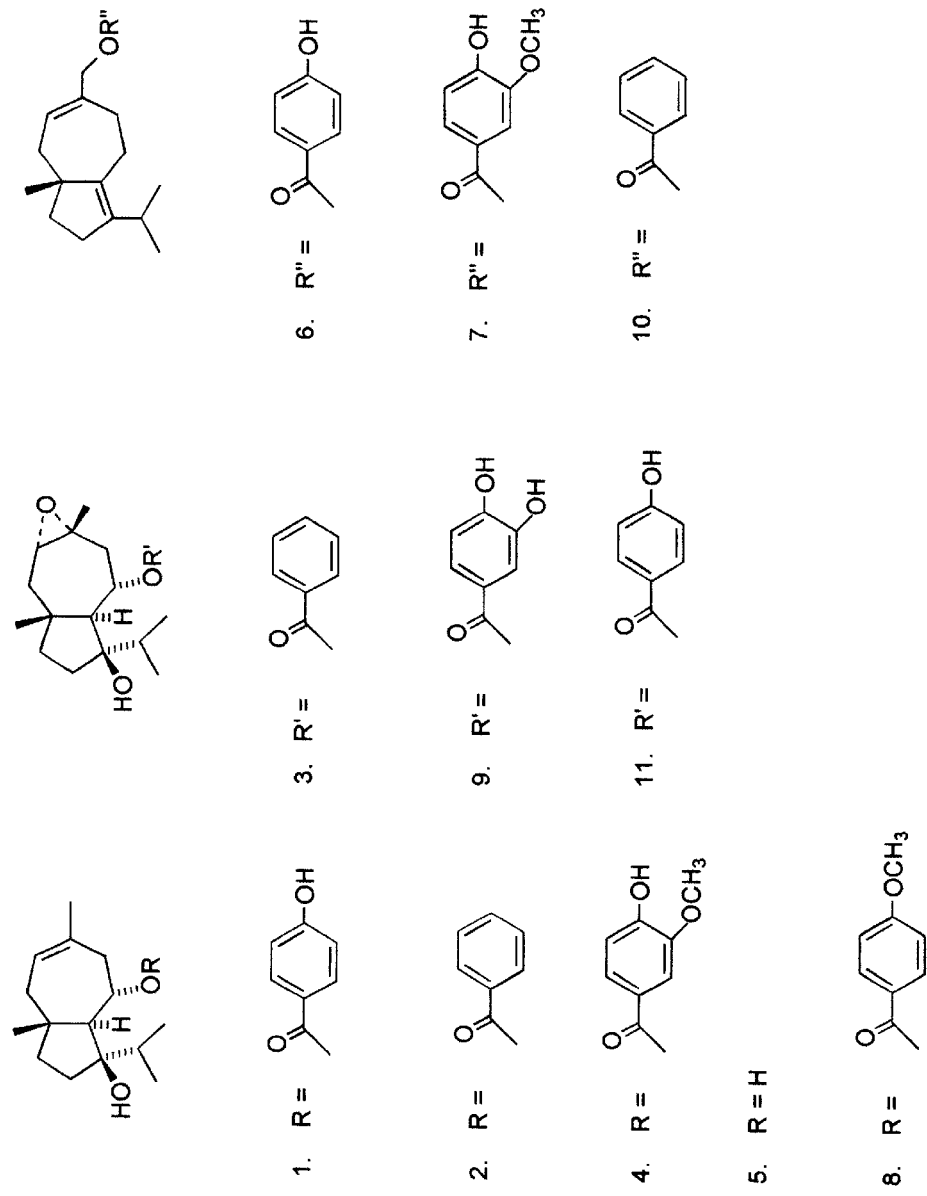
Figure 1. Structures of sesquiterpenes in the extracts of Ferula hermonis roots

PHARMACEUTICALLY ACTIVE COMPOSITION EXTRACTED FROM *FERULA HERMONIS* AND PROCESS OF ITS EXTRACTION

FIELD OF THE INVENTION

This invention relates to pharmaceutically active composition extracted from *Ferula hermonis* and process for its preparation using supercritical carbon dioxide.

BACKGROUND OF THE INVENTION

*Ferula hermonis* (known as Shirsh Zallouh) has recently received much attention due to its commercial value as an aphrodisiac, and as an herbal alternative to pharmaceutical drugs without the side effects. Shirsh Zallouh is the Arabic for "hairy root", a perennial of the parsley family. In northern Lebanon, Shirsh Zallouh is called Hashishat al-Kattira, which means herb of abundance. *Ferula hermonis* is a small shrub, with pale pink flowers. It grows at more than 6000 feet on the high mountain areas of northern Lebanon, and on the biblical Mount Hermon in Southern Lebanon, at the joint borders of Syria and Israel.

*Ferula hermonis* roots are usually picked in the summer, after they mature and before the snow-season. There are six different species of the plant Ferula, one of them contained the poison that killed the ancient Greek Philosopher Socrates. *Ferula hermonis* belongs to the family of plants known as the Umbelliferae. This family contains plants like the carrot, fennel, Chinese angelica and hemlock. Hemlock, of course, is extremely poisonous and there are reports that naïve ferula hunters are endangering their lives by picking hemlock, which is almost identical in appearance to Ferula.

Ferula genus constitutes about 150 species, and these are widely distributed throughout the Mediterranean area to central Asia. Medicinal properties of Ferula plants include antispasmodic, carminative, digestive, expectorant, sedative, antihysteric, laxative, aphrodisiac, antiseptic, and analgesic. The genus ferula species are rich in the sesquiterpenes daucanes, humulanes, carotanes, himachalanes, and guaianes.

*Ferula hermonis*' sexual potency was discovered by goat herders who noticed its strong sexual effects on their herds after eating this plant during the mating season. Middle East herbalists have used *Ferula hermonis* for centuries as a folk remedy to treat frigidity in women, and erectile and sexual dysfimction in men by increasing blood flow to sexual organs with dazzling results, and have reported renewed vigor, potency and energy. *Ferula hermonis* has been used by the elderly, in the Middle East for centuries to reinvigorate their sex lives.

In humans, the aphrodisiac property and safety of *Ferula hermonis* has been demonstrated in clinical trials involving more than 7,000 men with erectile dysfunction. The studies found that *Ferula hermonis* improved sexual function, increased libido and firmness of erections within few days. *Ferula hermonis* may work immediately for some, and may take few weeks for others. These trials revealed that 60 to 88 percent of men with erectile dysfunction experienced improved erections and increased desire within a few weeks after taking *Ferula hermonis* root; less than 4 percent experienced side effects such as headaches and flushing. The studies also found that *Ferula hermonis* may work almost immediately for some, and may take several weeks for others.

Because of the vasodilatation effects of *Ferula hermonis*, people with cardiovascular or neurological disorder should consult a heath care professional before taking this supplement. The common side effects associated with *Ferula hermonis* are headaches, flushing, and gastrointestinal tract.

Previous phytochemical investigations on *Ferula hermonis* revealed the presence of α-bisabolol and the daucane sesquiterpenes: 8,9-epoxy jaeschkeanadiol benzoate (epoxy ferutinol benzoate, (3)), jaeschkeanadiol vanillate (ferutinol vanillate, (4)), jaeschkeanadiol p-hydroxybenzoate (ferutinin, (1)), jaeschkeanadiol benzoate (Teferdin, (2)), jaeschkeanadiol (ferutinol, (5)), 8,9-epoxy jaeschjeanadiol (12), 14-(4 hydroxybenzoyloxy) dauc-4,8-diene (6), and 14-(4'-hydroxy-3'-methoxy-benzoyloxy) dauc-4,8-diene (7).

Ferutinine (1) and Tenuferidine (11) have been shown to have estrogenic activity, and may contribute to its aphrodisiac activity. Zallouh root also contains naturally occurring vitamins (A, B 1, B2, B6, C, D, and E) and minerals (iron, magnesium, selenium, and zinc).

A recent study found that Ferutinin, Ferutidin, and Tenuferidin increase cation permeability of lipid bilayers and mitochondria in a dose-dependent manner (Biochemica et Biophysica Acta. 2001; 1512:98-110).

It has been suggested that some components of Panoferol (a mixture of terpenoids from Ferula) may increase sex hormone levels and calcification rates, suggesting that panoferol acts on calcium homestasis. This suggestion was confirmed by the discovery that one of the panoferol mixture (Ferutinin) possesses $Ca^2$+ionophoric properties (Ignatkov V I, Ahmedhodzjaeva H T, Babichev V. effects of Tefestrol on the secretion of luteinizing hormone from the hypophysis. Farmakol Toksikol 1990; 53:37-38).

Ferutinin at concentration range 1 to 50 micromolar increased the permeability of thymocytes, mitochondria, sarcoplasmic reticulum, liposomes and bilayer lipid membranes for $Ca^2$+(Zamaraeva M V, Hagelgans A I, Abramov A Y, Ternovsky V I, Merzlyak P G, Tashmukhamedov B A, Saidkhodzjaev A. lonophoric properties of ferutinin. Cell calcium 1997; 22:235-241) Compounds Salpha-(3-methoxy-4-hydroxybenzoic acid) ester of jaeschjeanadiol, U and 5 alpha-(p-hydroxybenzoic acid) ester ofjaeschjeanadiol'were found to prevent pregnancy in adult female rats when administered orally on 1 to 7 post coitum. Compound Salpha-(3-methoxy-4-hydroxybenzoic acid) ester ofjaeschjeanadiol was found to be more potent than 5alpha-(p-hydroxybenzoic acid) ester ofjaeschjeanadiol since it prevented pregnancy in rats after a single oral administration of 5 mg per kg dose on the first day of post coitum. These two compounds also exhibited potent estrogenic activity. In an in-vitro assay to measure relative binding of these compounds to immature rat uterine cytosol estrogen receptors, these compounds exhibited relative binding affinity of 0.01 percent and 5.75 percent of 17 beta-estrodiol, respectively, for immature rat uterine cytosol estrogen receptors (Singh M M, Agnihotri A, Garg S N, Agarwal S K, Gupta D N, Keshri G, Kamboj V P. Antifertility and hormonal properties of certain carotane sesquiterpenes of Ferula jaeschkeana. Planta Medica 1988; 492).

In a recent study, the oil extracted from *Ferula harmonis* was found to enhance sexual activities as assessed by penile erection index in a dose dependent manner in male rats. The effective dose (12.03 mg/kg) was 880 times less than the lethal dose LD(50) (10.6 g/kg). This study also found that the *Ferula harmonis* extract becomes toxic if it is used for a long period of time (El-Thaher T S, Matalka K Z, Taha H A, Badwan A A. *Ferula harmonis* 'zallouh'and enhancing erectile function in rats: efficacy and toxicity study. Int J Impot Res 2001; 13:247-251).

The effects of *Ferula hermonis* extract on social aggression, fertility and some physiological parameters were examined in prepubertal male mice. Ingestion of 3 mg/kg of aqueous extract of *Ferula hermonis* for six weeks inhibited social aggression, and a significant reduction of their fertility. This treatment caused a significant decrease in the number of pregnant females, number of implantations and viable fetuses in females impregnated by males that ingested this extract (Khleifat K, Homady M H, Tarawneh K A, Shakhanbeh J. Effect of *Ferula hermonis* extract on social aggression, fertility and some physiological. parameters in prepubertal male mice. Endocr J 2001; 48:473).

The traditional way to take this herb is to slit the root and wait for the resin to ooze out. This process is now replaced by the more conventional organic solvent extraction procedure. Lebanese pharmacists cut up the root and make an extract by a hot alcohol extraction and distillation. It is recommended that men take 50 drops (two and half ml) of an alcohol (alcohol concentration of over ninety percent) extract of Zallouh root at night and again first thing in the morning. This regimen should be followed for at least four weeks. For women suffering from menstrual/menopausal complaints, 50 drops three times daily, after meals. The roots can also be soaked in wine or ground into powder and then taken in capsules or mixed with tea. In Syria, the powder is mixed with honey.

The suggested dose ranges from two to eight grams of Zallouh root taken as a tea. Some studies also indicated that a significant number of males experienced increased number of erections by taking Zallouh one to three hours prior to the anticipated sexual encounter.

The present invention overcomes the problem of using large effective dosage of *Ferula hermonis*, and provides a pharmaceutically active composition of *Ferula hermonis* free of solvent residue useful for small effective dosage and useful for formulation with other ingredients, and for formulation useful in different forms including soft and hard gel capsules and tablets, and clinical studies. The pharmaceutically active composition of *Ferula hermonis* free of solvent is obtained by supercritical fluid extraction.

The use of supercritical fluids for the extraction of chemical compounds from plants has received increasing attention because of the potential to dramatically reduce the time required for sample extraction as well as eliminating the need for large volumes of liquid solvents. Supercritical extraction is a technique in which gases are compressed under supercritical conditions to form a fluid, which is then used to remove chemicals from a matrix. Supercritical fluids have good extracting power because of their density, which can be controlled by changes in pressure or temperature, and to low viscosity, high diffusivity and low surface tension, which enhance mass transfer inside a solid matrix.

Carbon dioxide has a manageable critical point (i.e., critical pressure of 73 bar and critical temperature of 31 .degree. C.). At temperatures up to 31.06 degrees C. carbon dioxide can be liquefied by raising the pressure and this liquid exerts appreciable solvent power to dissolve natural oils and quite a wide range of non-polar or slightly polar materials. Supercritical carbon dioxide ($CO_2$) has been the most frequently used solvent in supercritical fluid extraction, being non-toxic, non-flammable, inexpensive and easily separated from extracts. Furthermore, the low critical temperature (31.06 degrees C.) of $CO_2$ allows extractions of heat sensitive compounds without degradation. As a result of these advantages, supercritical $CO_2$ fluid extraction has received increased attention as an alternative to conventional separation methods (see, e.g., Kirk-Othmer Encyclopedia of Chemical Technology, pages 872-893, Supplement volume, third edition, 1984, John Wiley and Sons, New York). Supercritical fluids have found myriad uses, including extracting oils, flavors, fragrances, and other materials from foods (Dziezak J.D., Innovative separation process finding its way into the food industry. *Food Technology* 1986; 40:66-9); in pharmaceutical industries (Bruno J, Castro C. A. N., Hamel, J. F. P., Palavra A.M.F. Supercritical fluid extraction of biological products. *In Recovery processesfor biological materials*, eds Kennedy J. F. and Cabral J. M. S., John Wiley & Sons, Chichester 1993, pp.303-54); and for the extraction of natural products (Extraction of natural products using near-critical solvents. Edited by King M. B. and Bott T. R. Published by Chapman and Hall, 1993; and Rui L. Mendes et al. Applications of supercritical carbon dioxide extraction to microalgae and plants. J Chem Tech Biotechnol 1995; 62:53-59).

Some of the food applications include de-caffeination of coffee and tea, hops, oil recovery and extraction of spices (Rizvi S. S. H., Daniels J.A., Benado A. L. and Zollweg, J.A., Supercritical fluid extraction: operating principles and food applications. Food Technology 1986; 40:57-64). Pharmaceutical applications include extraction of steroids (Larson K. A., and King M. L., Evaluation of supercritical fluid extraction in the pharmaceutical industry. Biotech. Prog 1986; 2:73-82) and chemotherapeutic alkaloids (Schaeffer S. T., Zalkow L. H., and Teja A. S., Extraction and isolation of chemotherapeutic pyrrolizidine alkaloids from plant substrates. ACS Symposium Series 1989; 406:416-33).

This technique has been used on an industrial scale for over two decades for the extraction of flavor principles from hops and other herbs. It has the advantage over extraction with conventional organic solvents that the extraction medium is readily and completely removed by allowing the liquid carbon dioxide to vaporize into the atmosphere. Thus, problems of waste solvent disposal and trace solvent contamination of finished product are eliminated. The uses of supercritical carbon dioxide for the preparation of plant extracts have been described in a number of U.S. patents.

U.S. Pat. No. 4,104, 409 described a process for extraction of the resin and essential oils of hops utilizing supercritical carbon dioxide fluid.

U.S. Pat. No. 6,180,105 disclosed a method of preparation of an artemisinin extract comprising the steps of extraction of Artemisia annua with liquid carbon dioxide and allowing the carbon dioxide to evaporate from the resultant mixture.

U.S. Pat. No. 6,319,524 disclosed a method of extracting saw palmetto berries by contacting ground saw palmetto berries with carbon dioxide at a pressure of at least 500 bar, and at a temperature of less than about 80 degrees C.

U.S. Pat. No. 6,117,431 described a method involving supercritical carbon dioxide to produce a purified extract from ginkgo biloba leaves.

U.S. Pat. No. 5,466,451 disclosed a process for extraction of pharmaceutically active compositions from the plant Tanacetum parthenium (Feverfew).

U.S. Pat. No. 5,591,343 disclosed a process for extraction of carotenoids from bacterial cells comprising the step of bringing the bacterial cells into contact with supercritical fluid so as to extract the carotenoids from the cells.

U.S. Pat. No. 6,111,108 described a method for extraction of biologically active components from the plant Camptotheca using supercritical carbon dioxide.

The present invention overcomes the problem of using large effective dosage of *Ferula hermonis*, and provides a pharmaceutically effective composition of *Ferula hermonis* free of solvent residue useful for small effective dosage and useful for formulation with other ingredients such as, but not limited to, sexual enahnacement, diabetic, weight management, hair, and tonic; useful formulation in different forms including soft and hard gel capsules and tablets; and clinical studies. The pharmaceutically active composition of *Ferula hermonis* free of solvent is obtained by supercritical fluid extraction.

SUMMARY OF THE INVENTION

It is an object of the invention to provide a pharmaceutically active composition from *Ferula hermonis*, said composition obtained by a process comprising fmely milling *Ferula hermonis*, and extracting the fmely milled *Ferula hermonis* with carbon dioxide in the supercritical state at a temperature from 31.degree to 80.degree. C. and under a pressure from 150 to 400 bar. According to a further aspect of the invention, the objects are achieved by providing a process for extracting a pharmaceutically active composition from *Ferula hermonis* said process comprising extracting finely milled *Ferula hermonis* with carbon dioxide in the supercritical state at a temperature from 31.degree to 80.degree. C. and under pressure from 150 to 400 bar.

It is also an object of the invention to provide a pharmaceutically active composition from *Ferula hermonis* containing terpenoid -like compounds as ingredients, which predominate in terms of amount.

It is also an object of the invention to provide a pharmaceutically active composition from *Ferula hermonis* for use in the preparation of pharmaceutical formulas, soft-drink, beverages, infusion, tablets, capsules, soft-gel capsules and dietary supplements.

Extracting is accomplished by flowing supercritical carbon dioxide through the powdered *Ferula hermonis* at an extraction pressure of at least about 150 bar. Those skilled in the art will recognize that a "bar" is a unit of pressure substantially equivalent to one atmosphere, or $10.\text{sup}.5$ newton/$m.\text{sup}.2$. Following extraction, the pharmaceutically active composition is separated from the carbon dioxide by decreasing the pressure to a predetermined separation pressure lower than the extraction pressure, and at a temperature sufficient to prevent the carbon dioxide from solidifying.

These objectives of the present invention will be more readily appreciated and understood from a consideration of the following detailed description.

BRIEF DESCRIPTION OF THE DRAWINGS

FIG. 1. Structures of sesquiterpenes in the extracts of *Ferula hermonis* roots

DETAILED DESCRIPTION OF THE INVENTION

Pharmaceutically active composition containing terpenoid-compounds from *Ferula hermonis* can be extracted through the use of organic solvents. Organic solvents, however, diffuse relatively slowly into and out of extractable substrates, rendering unduly long. Furthermore conventional extraction techniques involving liquid organic solvents afford a waste stream of solute-contaminated solvent that must be either recycled or disposed of. Due to these and other concerns supercritical fluid extraction of terpenoids from *Ferula hermonis* is used as a replacement of conventional solvent extraction processes.

A supercritical fluid is a fluid at a temperature above its critical value. A supercritical fluid has properties, which are intermediate between those of gases and liquids. It has a viscosity, which is higher than that of a gas. These properties allow supercritical fluids to penetrate matrices easily, while retaining reasonable dissolving power.

The process of the invention involves the use of a supercritical fluid comprising supercritical carbon dioxide ($CO_2$) as a means of separating pharmaceutically active composition containing terpenoid-compounds from *Ferula hermonis*. The process of the invention can be carried out in any environment suitable for containing the supercritical fluid in contact with *Ferula hermonis*. Operating parameters for a process of the invention are limited by the minimum temperature and pressure required for the supercritical phase for $CO_2$ (critical density is 470 $kg/m^3$, critical pressure is 73 bar, critical temperature 30.1 degree.C.).

Suitable conditions (time of contact between *Ferula hermonis* and the supercritical fluid, temperature, and pressure) can be readily selected by those skilled in the art. It is well known that supercritical fluids exhibit increasing solvent power with increasing pressure (i.e. increasing fluid density). The solvent power of supercritical $CO_2$ can be readily tailored by adjusting the temperature and pressure of the supercritical phase such that the desired chemical compounds (terpenoids) be dissolved and removed from the *Ferula hermonis*.

According to the present invention, extraction is carried out in a pressure-resistant container by bringing a supercritical carbon dioxide fluid into contact with *Ferula hermonis* powder to be extracted.

Any extraction temperature the same as or higher than the critical temperature of the supercritical fluid used can be used. For carbon dioxide, the extraction temperature is same as or higher than the critical temperature of carbon dioxide, i.e., 31.degree. C., and usually up to 100.degree. C., more preferably up to 60.degree. C., and even more preferably up to 40.degree. C.

Any extraction pressure is the same as or higher than the critical pressure of supercritical carbon dioxide, i.e., 73 bar and usually up to 500 bar, and preferably 200 bar.

Numerous modifications and variations of the present invention are possible in light of the above teachings. It is therefore to be understood that within the scope of the attendant claims attached hereto, this invention may be practiced otherwise than as specifically disclosed herein.

As will be apparent to persons skilled in the art, modifications and adaptations to the above-described invention can be made without departing from the spirit and scope of the invention.

The pharmaceutically active composition containing terpenoid-compounds obtained by supercritical carbon dioxide fluid extraction was analyzed by Liquid chromatography/mass spectroscopy (LC/MS). LC/MS method was used for the determination and profiling of the daucane sesquiterpenes in *Ferula hermonis* extracts. The LC/MS of the extract showed the presence of the sesquiterpenes jaeschkeanadiol benzoate (Teferdin, (2)), 8,9-epoxy jaeschkeanadiol benzoate (epoxy ferutinol benzoate, (3)), jaeschkeanadiol vanillate (ferutinol vanillate, (4)), jaeschkeanadiol (ferutinol, (5)), 14-(4 -hydroxybenzoyloxy) dauc-4,8-diene (6), 14-(4'-hydroxy-3'-methoxy-benzoyloxy) dauc-4,8-diene (7), jaeschkeanadiol p-methoxy benzoate (Ferutidine, (8)), 8,9-epoxy jaeschkeanadiol m,p dihydroxy benzoate (9), 14-benzoyloxy dauc-4,8-diene (10), and 8,9-epoxy jaeschkeanadiol p-hydroxy benzoate (11).

In a recent study on HPLC analysis of *Ferula hermonis*, compunds (1), (2), (3), and (4) were quantified as the marker daucane sesquiterpenes esters, with (I) and (2) as the major components [6].

LC/MS analyses were performed with a Platform II APCI Mass Spectrometer (Micromass, Inc., Beverly, Mass.) interfaced with a Gilson 215 Liquid Chromatograph with UV detection. The mass spectrometer was operated in a continuous scanning mode over a mass range of 120 to 1600 amu using an APCI probe. The chromatographic separations were achieved with a Genesis reversed C1 8 analytical column (15 cm, 2.1 mm I.D., 4 pm particle size, Genesis, Jones Chromatography). Samples (50μ) were eluted using a gradient of water containing 1% (by volume) formic acid to acetonitrile containing 1% (by volume) formic acid at a flow-rate of 0.5 ml/min, over 16 minutes. Quantification was carried out at 254 un.

Development of accurate quantitative profile of analysis for specific marker compounds in herbal manufacturing is critical for determining the quality and consistency of raw materials and finished products, to ensure the desired health benefit and to reliably examine their efficacy in clinical studies. To identify the individual peaks in the HPLC chromatogram of the Ferula hermonis extract, LC-atmospheric pressure chemical ionization in both the positive and negative mode MS analyses were employed.

Tables (1) shows the pertinent parameters of the LCIMS analyses. In accordance with previous phytochemistry studies, the mass spectrum of the Ferula hermonis extract showed peaks in the positive ion mode at m/z 341 and 371 corresponding to compounds (6) and (7), respectively; and peaks in the negative mode at m/z 341, 357 and 387 corresponding to compounds (2), (3) and (4), respectively. The peak at m/z 357 could also be assigned to compound (1), both (1) and (3) were previously observed by Galal and coworkers, who reported (1) as the minor and (3) as the main components in the Ferula hermonis extract; (3) was eluted at a longer time than (1) on a reversed phase C18 column. On the basis of these observations, we assigned the peak at m/z 357 to compound (3).

In addition, ions not previously reported for Ferula hermonis were also observed at m/z 325 in the positive mode; and 373, 371 and 389 in the negative mode, which we tentatively assigned to the sesquiterpenes (10), (11), (8), and (9), respectively. This class of sesquiterpenes has been previously reported in the genus ferula. An unknown peak at m/z 373 (positive mode) was also observed.

All the peaks at m/z 341, 371 and 325 in the positive mode showed m/z 203 corresponding to M-ester, 122 for benzoate, 168 for vanillate, and 138 for p-hydroxybenzoate, respectively.

In a recent study, Ferutinin (1), Ferutidin (8), and Tenuferidin (11) were found to increase cation permeability of lipid bilayers and mitochondria in a dose dependent manner, suggesting that these sesquiterpenes may increase hormone levels.

Preferred methods involve extraction at a pressure of 100 to 310 bars (1500 to 4500 psi), preferably about 200.bar (3000 psi) and at a temperature in the region of 31 to 80 degrees C., preferably 40 degrees C. The invention is further described by means of an example but not in any limitative sense.

EXAMPLE

Roughly ground roots of Ferula hermonis were packed into a pressure vessel. A volume of liquid carbon dioxide at the ratio of approximately 30 ml of liquid carbon dioxide per 1 g of Ferula hermonis roots was allowed to pass through the raw material. The residual extract in the collection vessel was gummy. The following extraction conditions were employed:

| Pressure | Temperature | % Yield |
| --- | --- | --- |
| 200 bar | 40 degree. C. | 10 to 20 |

This process allows not only for custom blends to meet specific consumer demands, but also for a great degree of standardization of the product. The invention provides a Ferula hermonis composition preferably for nutritional supplementation. The invention allows for nutritional supplementation ingesting a composition comprising essentially no solvent residue.

Literature Cited

[1] Al-Yahia M A, Muhammad I, Mirza H H, E l-Feraly F S. Antibacterial constituents from the rhizomes of Ferula cummunis. Phytother. Res 1998; 12:335-339

[2] Ahmed A A. Daucanes and other constituents from Ferula sinaica. Phytochemistry 1991; 30:1207-1210

[3] El-Thaher T S, Matalka K Z, Taha HA, Badwan AA. Ferula Harmonis 'Zallouh'and enhancing erectile function in rat efficacy and toxicity study. Int J Impot Res 2001; 13:247-51

[4] Galal A. Sesquiterpenes from Ferula hermonis Boiss. Pharmazie 2000; 55:961-962

[5] Galal AM, Abourashed EA, Ross SA, ElSohly MA, Al-Said, MS, El-Feraly FS. Daucane sesquiterpenes from Ferula hermonis. J Nat Prod 2001; 64:399-400

[6] Abourashed EA, Galal AM, El-Feraly, Khan IA. Separation and quantification of the major Daucane esters of Ferula hermonis by HPLC. Planta Med 2001; 67:681-682

[7] Razdan TK, Qadri B, Qurishi MA, Khuroo MA, Kachroo PK. Sesquiterpene esters and sesquiterpenes-coumarin esters from Ferula Jaeskeana. Phytochemistry 1989; 28:3389-3393

[8] Abramov AY, Zamaraeva MV, Hagelgans Al, Azimov RR, Krasilnikov OV. Influence of plant terpenoids on the permeability of mitochondria and lipid bilayers. Biochimica et Biophysica Acta 2001; 1512:98- 110.

What is claimed is:

1. A pharmaceutically active composition extracted from Ferula hermonis roots by a process comprising a) finely milling Ferula hermonis, b) extracting the pharmaceutically active composition from said milled Ferula hermonis with a supercritical fluid, c) recovering the pharmaceutically active composition from the supercritical fluid.

2. The pharmaceutically active composition of claim 1, wherein the composition consists of terpenoid-compounds.

3. The pharmaceutically active composition of claim 1, wherein the composition comprising the terpenoid-compounds: jaeschkeanadiol benzoate 8,9-epoxy jaeschkeanadiol benzoate jaeschkeanadiol vanillate, jaeschkeanadi 14-(4 '-hydroxybenzoyloxy) dauc-4,8-diene14-(4'-hydroxy-3 'methoxy-benzoyloxy) dauc-4,8-diene, jaeschkeanadiol p-methoxy benzoate 8,9-epoxy jaeschkeanadiol m,p-dihydroxy benzoate; 14-benzoyloxy dauc-4,8-diene, and 8,9-epoxy jaeschkeanadiol p-hydroxy benzoate.

4. The process of claim 1, wherein Ferula hermonis is milled at 25 degrees C. to a particle size between 50 to 100 mesh.

5. The process of claim 1, wherein the supercritical fluid is carbon dioxides.

6. The process of claim 1, wherein the pharmaceutically active composition is extracted by contacting said milled *Ferula hermonis* with a continuous flow of supercritical carbon dioxide under conditions and for a time sufficient to remove the composition from *Ferula hermonis*.

7. The process of claim 1, wherein the supercritical carbon dioxide fluid extraction is performed at temperatures ranging from 31 to 80 degree C. and pressures between 150 and 400 bar.

8. The process of claim 1, wherein the supercritical carbon dioxide fluid extraction is performed at 40 degree C., and 200 bar.

9. The process of claim 1, wherein the supercritical carbon dioxide to feed ratio ranges 10:1 to 100:1.

10. The process of claim 1, wherein the extraction consists essentially of using supercritical carbon dioxide without other extracting agents.

11. The pharmaceutically active composition of claim 1, wherein the composition is provided in a form selected from the group consisting of a soft gelatin capsule, a hard gelatin capsule, a liquid, powder, granules, a tablet, an ointment, a food and delay supplements.

12. The process of claim 1, wherein the supercritical carbon dioxide to feed ratio ranges 30:1.

* * * * *